United States Patent
Wallace et al.

(10) Patent No.: US 10,266,347 B2
(45) Date of Patent: Apr. 23, 2019

(54) CONVEYOR BELT EDGE DETECTION SYSTEM

(71) Applicant: ContiTech Transportbandsysteme GmbH, Hannover (DE)

(72) Inventors: Jack Wallace, Powell, OH (US); Jacques Basson, Durban (ZA)

(73) Assignee: ContiTech Transportbandsysteme GmbH, Hannover (DE)

( * ) Notice: Subject to any disclaimer, the term of this patent is extended or adjusted under 35 U.S.C. 154(b) by 0 days.

(21) Appl. No.: 15/761,932

(22) PCT Filed: Sep. 20, 2016

(86) PCT No.: PCT/US2016/052561
§ 371 (c)(1),
(2) Date: Mar. 21, 2018

(87) PCT Pub. No.: WO2017/058557
PCT Pub. Date: Apr. 6, 2017

(65) Prior Publication Data
US 2018/0273303 A1   Sep. 27, 2018

Related U.S. Application Data

(60) Provisional application No. 62/235,145, filed on Sep. 30, 2015.

(51) Int. Cl.
*B65G 43/02* (2006.01)
*G01N 27/82* (2006.01)

(52) U.S. Cl.
CPC ............ *B65G 43/02* (2013.01); *G01N 27/82* (2013.01)

(58) Field of Classification Search
CPC ... B65G 43/02; B65G 43/06; B65G 2203/043
USPC .......................... 198/810.01, 810.02, 810.03
See application file for complete search history.

(56) References Cited

U.S. PATENT DOCUMENTS

| | | | |
|---|---|---|---|
| 3,651,506 A | 5/1972 | Olaf et al. | |
| 4,621,727 A | 11/1986 | Strader | |
| 4,864,233 A | 9/1989 | Harrison | |
| 6,264,577 B1 * | 7/2001 | Hutchins | B60C 23/0493 198/502.1 |
| 6,291,991 B1 * | 9/2001 | Schnell | B65G 43/02 198/810.02 |
| 7,954,632 B2 * | 6/2011 | Kropf-Eilers | B65G 15/32 198/502.1 |

(Continued)

*Primary Examiner* — James R Bidwell
(74) *Attorney, Agent, or Firm* — David L. Cate

(57) ABSTRACT

A conveyor belt (8) and method for monitoring a moving conveyor belt (8), the conveyor belt (8) having a first edge region (2), a second edge region (4), and a load carrying region (6). The method functions to detect belt edge damage, changes in belt width, and changes in belt tracking by monitoring a magnetic field associated with a plurality of edge detection inserts (1,3) embedded within the conveyor belt (8). In one embodiment this is achieved by monitoring images of the magnetic field associated with the edge detection inserts (1,3) embedded within the conveyor belt (8). The method may utilize a magnetic sensor system to detect magnetic images of the edge detection inserts (1,3) where the edge detection inserts (1,3) are positioned longitudinally along the length of the conveyor belt (8) in the first edge region (2) and the second edge region (4) of the conveyor belt (8).

15 Claims, 3 Drawing Sheets

(56) References Cited

U.S. PATENT DOCUMENTS

| | | | |
|---|---|---|---|
| 8,025,144 B2 * | 9/2011 | Lewis | G09F 19/22 198/618 |
| 2010/0145631 A1 | 6/2010 | Alport et al. | |
| 2015/0144459 A1 | 5/2015 | Wallace et al. | |

* cited by examiner

CONVEYOR BELT EDGE DETECTION SYSTEM

RELATED APPLICATION INFORMATION

This patent application claims priority to U.S. Provisional Patent Application No. 62/235,145 filed Sep. 30, 2015, and Patent Cooperation Treaty (PCT) Patent Application No. PCT/US2016/052561 filed Sep. 30, 2016, the disclosures of which are incorporated herein in their entirety, by reference.

FIELD

The field to which the disclosure generally relates is conveyor belts, and more particularly to detecting conveyor belt edge damage, changes in conveyor belt width, and changes in conveyor belt tracking.

BACKGROUND

This section provides background information to facilitate a better understanding of the various aspects of the disclosure. It should be understood that the statements in this section of this document are to be read in this light, and not as admissions of prior art.

A multitude of commercial applications are available for heavy-duty conveyor belts which transport products and materials, including minerals, coal, and a wide variety of manufactured products from one point to another. Such conveyor belts can include buckets or corrugated walls to facilitate transportation of certain materials. In many cases the conveyor belts are relatively long, extending over a distance of several miles, and they can represent a high cost component of an industrial material handling operation. The conveyor belts and their respective drives are susceptible to normal wear and tear as well as damage from the material being transported, and/or harsh environmental conditions. In the event the conveyor belt suffers catastrophic damage or otherwise becomes inoperable, the costs of repairing the conveyor belt, cleaning up any spilled material, and related downtime are substantial. For instance, sharp edges of the material being transported can gouge the surface of the belt and that can result in a rip developing.

When a rip or damaging event is detected, the belt can often be repaired. Where the belt damage is not detected and repaired promptly, the rip typically propagates along the length of the belt with continued use of the conveyor system and this renders the repair even more difficult and costly. It is accordingly desirable to detect damage to the belt as soon as possible after it occurs and to quickly repair the damaged area of the belt. By doing so the extent of the damage to the belt can be minimized and the spillage of material being conveyed can be reduced.

Over the years, a number of systems have been developed for detecting belt damage and for automatically stopping further movement of the belt after the damage occurs. It is well known to employ sensors within conveyor belts as part of a rip detection system. In a typical system, sensors in the form of loops of conductive wire are affixed or embedded in the belt and provide a rip detection utility as part of an overall rip detection system. Rip detection is achieved through the inferential detection of an "open circuit" condition in one or more of the sensor loops in the belt. Typically, an electrical energy source external to the belt is inductively or capacitively coupled to a sensor loop in the belt. A break in the conductive wire loop of the sensor may be detected by a remote transmitter/receiver (exciter/detector). Disposition of a plurality of such sensors at intervals along the conveyor may be effected with each sensor passing within read range of one or more exciter/detectors at various locations. A rip or tear will encounter and damage a proximal sensor loop and the existence of the tear will be detected when the proximal sensor loop damage is detected as an open circuit by the reader at its next pass. In this manner, the existence of a tear will be promptly detected and repaired with further damage to the belt being minimized.

U.S. Pat. No. 8,256,607 discloses a sensor system for a conveyor belt in which a monitoring system is provided for a moving conveyor belt having a plurality of embedded reinforcing cords and identification tags. A tag reader detects and identifies the identification tags passing by the tag reader while a belt monitor scans the cords to detect a plurality of magnetic reference points and a damage event of at least one cord. A control unit in communication with the belt monitor and the tag reader analyzes the belt monitor to identify the plurality of magnetic reference points and the damage event. The control unit also acquires a belt location on the moving conveyor belt from a belt map based on the detected and identified identification tag and a magnetic reference point from the plurality of magnetic reference points. When a damage event is identified, a location of the damage event is determined by the control unit based on the acquired belt location.

U.S. Pat. No. 8,069,975 discloses a conveyor belt rip detection system which provides a conveyor belt rip detection system with belts having rip detection inserts that can be more easily integrated into conveyor belts at low cost. These rip detection inserts do not adversely affect the durability of the conveyor belt and can be easily replaced in the event of belt damage. This rip detection system also provides a highly reliable early image of belt damage that can facilitate quick repair before extensive belt damage occurs. The present disclosure more specifically discloses a conveyor belt comprising (1) an elastomeric body having a load carrying surface and a parallel pulley engaging surface; (2) a reinforcement ply disposed within the elastomeric body; and (3) a multitude of rip detection inserts, wherein the rip detection inserts are spaced along the longitudinal length of the conveyor belt, wherein the rip detection inserts contain a multitude of rip detection wires that are comprised of a magnetically permeable material, wherein the rip detection wires are aligned in the rip detection inserts at a bias angle of 15° to 75° from being perpendicular to the longitudinal direction of the belt, and wherein the rip detection wires are spaced incrementally across the width of the belt.

U.S. Pat. No. 7,810,634 discloses a sensor system for a conveyor belt in which a monitoring system is provided for a moving conveyor belt having a plurality of embedded reinforcing cords and identification tags. A tag reader detects and identifies the identification tags passing by the tag reader while a belt monitor scans the cords to detect a plurality of magnetic reference points and a damage event of at least one cord. A control unit in communication with the belt monitor and the tag reader analyzes the belt monitor to identify the plurality of magnetic reference points and the damage event. The control unit also acquires a belt location on the moving conveyor belt from a belt map based on the detected and identified identification tag and a magnetic reference point from the plurality of magnetic reference points. When a damage event is identified, a location of the damage event is determined by the control unit based on the acquired belt location.

Prior art rip detection systems do not provide sufficient detection means to alert conveyor belt operators to damage occurring at the longitudinal edges of a conveyor belt. This region of the belt is especially critical to bucket conveyor belts, conveyor belts employing corrugated walls, and fabric belts generally. Damage to belt edges of any type of conveyor belt can lead to transverse tearing, which can cause products or materials to fall or become damaged, and the repair of such tearing can be costly and time consuming. Furthermore, prior art detection systems do not sufficiently detect conveyor belt tracking failures in which a conveyor belt veers from a designated track during belt operation. When a belt is removed a given distance from its track, the belt itself and the property carried upon it can be damaged. Additionally, stringers, idlers and other supporting structures can be also damaged if the belt tracks too far out of proper alignment. There is accordingly a need for a conveyor belt edge detection system which can also be used to monitor belt tracking during conveyor belt operation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Aspects of this disclosure resolve deficiencies of the prior art by offering conveyor belt operators a conveyor belt and conveyor belt monitoring system capable of detecting conveyor belt width changes, edge tracking failures, and belt edge damage. The magnetic wiring utilized in this system is flexible to withstand strain on the belt. Rip detection inserts can optionally be placed throughout the center of the conveyor belt for added rip detection. Conveyor belts made from elastomeric materials, fabrics, combinations, and the like can benefit from this disclosure. In some cases, such components are applied to walled conveyor belts, conveyor belts having corrugated sidewalls, and to bucket conveyor belts. However, these concepts are applicable to a wide variety of conveyor belts of various designs.

In some embodiments of this disclosure the conveyor belt is comprised of a load carrying surface, a pulley engaging surface, a reinforcement ply disposed within the belt, magnetic rip detection inserts embedded within the center region of the belt, and a multitude of edge detection inserts. The belt can be comprised of one or more plies, which are typically arranged in a woven pattern to add strength to the belt. The edge detection inserts are adapted to facilitate monitoring the integrity of the conveyor belt edges and to track the position of the belt edges relative to a magnetically designed base map image which exemplifies a normal belt in normal operation. The base map is used as a baseline from which deviations can be indicative of variations in the alignment of the belt in the conveyor system and/or belt damage.

In some embodiments, the present disclosure provides a conveyor belt comprising a load carrying surface, a pulley engaging surface, a reinforcement ply disposed within the belt, magnetic rip detection inserts embedded in the center region of the belt, and a multitude of edge detection inserts embedded in a first edge region and a second edge region of the conveyor belt. The edge detection inserts are adapted to facilitate monitoring the integrity of the conveyor belt edges and to track the position of the belt edges relative to a base map within the conveyor system. The edge detection inserts would be located within the first edge region and the second edge region on the conveyor belt. The first edge region and the second edge region of the conveyor belt do not extend across more than about 45% of the total width of the conveyor belt. The edge detection inserts extend longitudinally and continuously along the length of the belt and the edge detection inserts contain a plurality of magnetically permeable wires. In some embodiments, the rip detection inserts are between 30 to 50 centimeters wide. In some embodiments, the edge detection inserts are between 12 centimeters to 17 centimeters wide, and the edge detection inserts are spaced incrementally along the longitudinal edges of the conveyor belt.

In some aspects, the magnetically permeable wires are aligned in the edge detection inserts at a bias angle of 0° to 90° from being perpendicular to the longitudinal direction of the belt, at a bias angle of 15° to 75° from being perpendicular to the longitudinal direction of the belt, at a bias angle of 25° to 65° from being perpendicular to the longitudinal direction of the belt, or even at a bias angle of 35° to 55° from being perpendicular to the longitudinal direction of the belt. Also, in some cases, the first edge region and the second edge region of the conveyor belt do not extend across more than 30% of the total width of the conveyor belt, more than 25% of the total width of the conveyor belt, or even more than 20% of the total width of the conveyor belt.

In some embodiments of the disclosure, the conveyor belts include corrugated walls, and may have a first corrugated wall situated between the load carrying region and the first edge region of the conveyor belt, and a second corrugated wall is situated between the load carrying region and the second edge region of the conveyor belt. The conveyor belts may also be bucket conveyor belts, which may include a plurality of buckets situated within the load carrying region of the conveyor belt.

The present disclosure also discloses a method for monitoring a moving conveyor belt to detect belt damage, changes in belt width, and changes in belt tracking. The method comprises monitoring a moving conveyor belt having a first edge region, a second edge region, and a load carrying region. The conveyor belt can be monitored using images of a magnetic field associated with a plurality of edge detection inserts embedded within the conveyor belt. The magnetic image can be generated by taking the amplitude of one or more components of the magnetic field at a fixed distance from the surface of the conveyor belt. In such cases, a magnetic sensor system would detect the magnetic images of the edge detection inserts positioned longitudinally along the length of the conveyor belt. The edge detection inserts would fall within the first edge region and the second edge region of the conveyor belt, and the edge detection inserts would contain a plurality of magnetically permeable wires. In an alternative embodiment of this disclosure a single line chart can be compared against a baseline rather than detecting the full magnetic image associated with the edge detection inserts.

In the practice of some embodiments of this disclosure the integrity of the rip insert panels in the edges of the conveyor belt are monitored to detect the occurrence of possible belt edge damage. Also, magnetic signatures along the length of the conveyor belt can be monitored to determine tracking relative to the sensor array which can provide alerts warning of improper tracking of the belt in the conveyor system. This disclosure also provides the ability to detect width changes in the belt by monitoring the position of the edges of the belt relative to each other and relative to fixed points in the conveyor system.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and wherein.

DETAILED DESCRIPTION

The following description of the variations is merely illustrative in nature and is in no way intended to limit the scope of the disclosure, its application, or uses. The description and examples are presented herein solely for the purpose of illustrating the various embodiments of the disclosure and should not be construed as a limitation to the scope and applicability of the disclosure. In the summary of the disclosure and this detailed description, each numerical value should be read once as modified by the term "about" (unless already expressly so modified), and then read again as not so modified unless otherwise indicated in context. Also, in the summary of the disclosure and this detailed description, it should be understood that a value range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors had possession of the entire range and all points within the range.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of concepts according to the disclosure. This description should be read to include one or at least one and the singular also includes the plural unless otherwise stated.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

Figure 1:
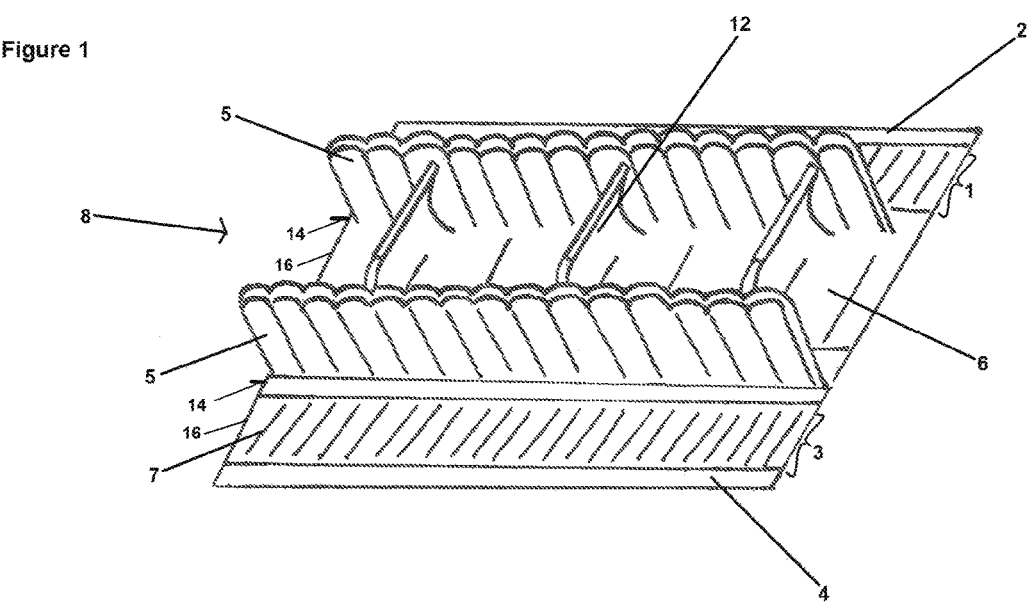
FIG. 1 shows aspects of the disclosure applied to a conveyor belt having corrugated walls, in a perspective view.

The present disclosure includes a conveyor belt and a conveyor belt monitoring system. FIG. 1 depicts one embodiment of this disclosure in which a conveyor belt 8 has corrugated walls 5, cleats 12, a first edge region 2, and second edge region 4, and a load carrying region 6. Generally the edge regions 2, 4 do not extend across more than 45% of the total width of the conveyor belt. Typically the edge regions 2, 4 do not extend across more than 35% of the total width of the conveyor belt. Commonly the edge regions 2, 4 do not extend across more than 30% of the total width of the conveyor belt. In some cases, the edge regions 2, 4 do not extend across more than 20% of the total width of the conveyor belt.

FIG. 1 further shows a first edge detection insert 1 located in the first edge region 2 of the conveyor belt 8, and a second edge detection insert 3 located in the second edge region 4 of the belt 8. In this embodiment the edge detection inserts 1, 3 are located on the outside of the corrugated walls 5. In other words, a first corrugated wall 5 is situated between the load carrying region 6 and the first edge region 2 of the conveyor belt 8, and a second corrugated wall 5 is situated between the load carrying region 6 and the second edge region 4 of the conveyor belt 8. Only two edge detection inserts 1, 3 are shown in FIG. 1, but any conveyor belt utilizing this disclosure can have several edge detection inserts longitudinally spaced discontinuously and incrementally throughout the belt edges. In some embodiments of this disclosure, the edge detection inserts will be spaced apart based upon the location of the conveyor belt steel cable 14 and splices 16 in order to provide the edge detection inserts with a unique magnetic characteristic that can be more readily detected by sensors.

The conveyor belt 8 edge detection inserts 1, 3 sit longitudinally along the length of the belt for a distance of at least one meter. Typically, the edge detection inserts 1, 3 are between 12 to 17 centimeters wide, and between 1 to 10 meters in length. The size of the edge detection inserts 1, 3 will depend on the design and width of the conveyor belt.

The edge detection inserts 1, 3 contain a plurality of magnetically permeable wires 7. Generally the magnetically permeable wires 7 are aligned within the edge detection inserts 1, 3 at a bias angle of from about 0° to about 90° from being perpendicular to the longitudinal direction of the belt, or even from about 15° to about 75° from being perpendicular to the longitudinal direction of the belt. Typically the magnetically permeable wires 7 are aligned within the edge detection inserts 1, 3 at a bias angle of from about 25° to about 65° from being perpendicular to the longitudinal direction of the belt. Preferably the magnetically permeable wires 7 are aligned within the edge detection inserts 1, 3 at a bias angle of from about 35° to about 55° from being perpendicular to the longitudinal direction of the belt.

Figure 2:
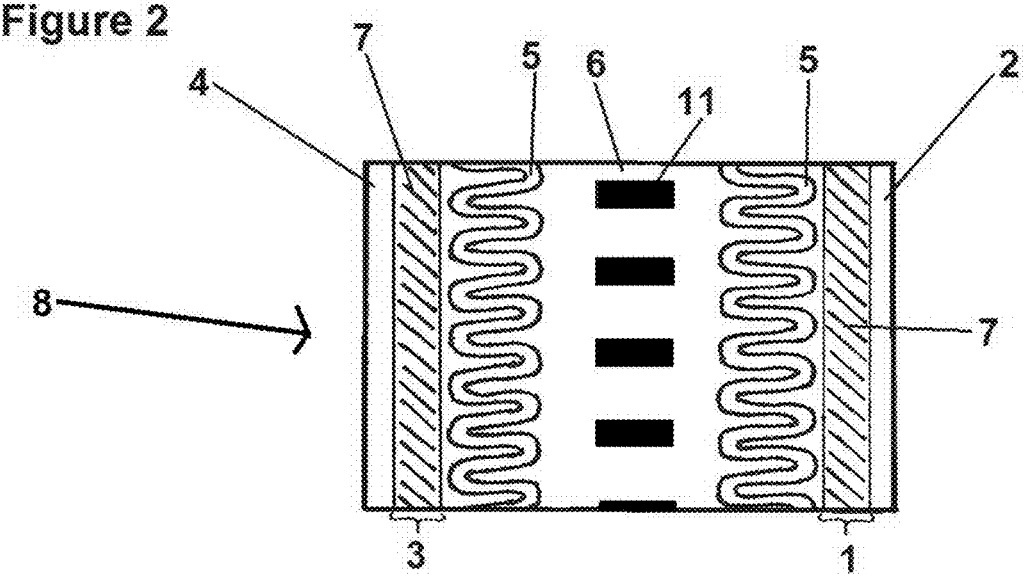
FIG. 2 illustrates aspects of the disclosure applied to a conveyor belt having corrugated walls, in an aerial view; and, FIG. 3 depicts aspects of the disclosure applied to bucket conveyor belt, in a perspective view.

FIG. 2 provides an aerial view of the conveyor belt 8 having corrugated walls 5. As in FIG. 1, this view shows the conveyor belt 8 having two edge detection inserts 1, 3 with magnetically permeable wires 7 located within the belt edge regions 2, 4. In this embodiment the conveyor belt 8 includes conventional rip detection inserts 11 embedded within the load carrying region 6. The rip detection inserts 11 are usually between 30 to 50 centimeters wide, and in some cases, between 40 to 45 centimeters wide.

Conventional rip detection inserts and rip detection systems which can be utilized in conjunction with this disclosure include those described in U.S. Pat. Nos. 8,069,975, 8,256,607, 7,942,258, 7,894,934, 7,810,634, and 7,740,130. The teachings of U.S. Pat. No. 8,069,975, 8,256,607, 7,942,258, 7,894,934, 7,810,634, and 7,740,130 are incorporated herein by reference for the purpose of teaching techniques for detecting rips using conventional rip detection inserts in the load carrying regions of belts which can be utilized in accordance with this disclosure. The teachings of these prior art references are also incorporated by reference for the purpose of showing conveyor systems and detection systems which utilize magnetic imaging systems which can be employed in conjunction with the belts of this disclosure which include edge detection inserts.

Figure 3:
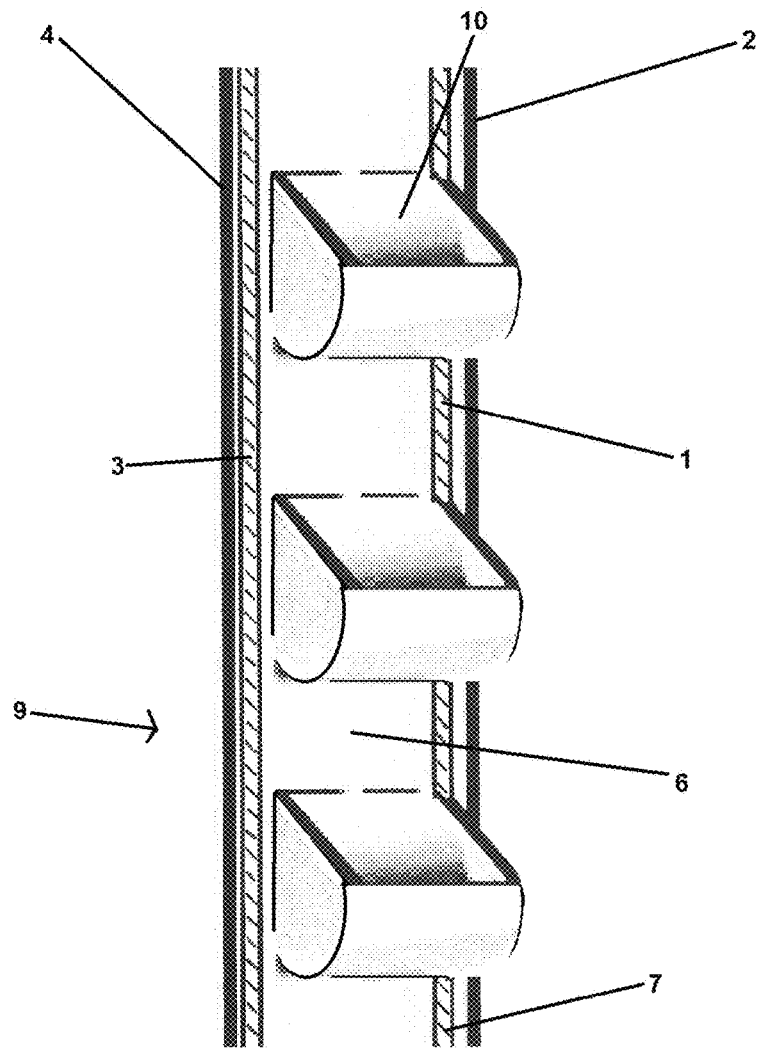

FIG. 3 shows one embodiment of this disclosure using a bucket conveyor belt 9. The bucket conveyor belt also has two edge detection inserts 1, 3 with magnetically permeable wires 7 located within the belt edge regions 2, 4. The conveyor belt buckets 10 sit within the load carrying region 6 of this conveyor belt, and the edge detection inserts 1, 3 are embedded into the conveyor belt 9 on the outside of the belt buckets 10. In the case of bucket conveyors the edge portions of the belt carry virtually the entire load of the system and are hence critical to system functionality.

The edge detection inserts utilized in this disclosure are adapted to facilitate monitoring the integrity of the conveyor belt edges and to track the position of the belt edges relative to a base map within the conveyor monitoring system. Monitoring the conveyor belt is accomplished by using a sensor to scan the moving belt and detect the magnetically permeable wires 7 within the multitude of edge detection inserts 1, 3 located within the belt edge regions 2, 4. In one embodiment of this disclosure the magnetic field extends over the length of the conveyor belt. After the edge detection inserts 1, 3 are scanned, data from the scanned edge detection inserts 1, 3 is analyzed to identify belt damage, changes in belt size, and deviations in the position of the conveyor belt along the belt track. In other words, sensors would scan the moving conveyor belt to generate images of the moving conveyor belt based upon the magnetically permeable wires 7 within the edge detection inserts 1, 3, and the image generated using conveyor belt sensors would be compared to the belt base map to detect any aforementioned belt damage, changes in belt size, and deviations of the belt from the belt track.

LIST OF REFERENCE SIGNS (PART OF THE DESCRIPTION)

1 Edge Detection Insert
2 Belt Edge Region
3 Edge Detection Insert
4 Belt Edge Region
5 Corrugated Walls
6 Load Carrying Region
7 Magnetically Permeable Wires
8 Conveyor Belt
9 Bucket Conveyor Belt
10 Conveyor Belt Buckets
11 Rip Detection Inserts
12 Cleats The foregoing description of the embodiments has been provided for purposes of illustration and description. Example embodiments are provided so that this disclosure will be sufficiently thorough, and will convey the scope to those who are skilled in the art. Numerous specific details are set forth such as examples of specific components, devices, and methods, to provide a thorough understanding of embodiments of the disclosure, but are not intended to be exhaustive or to limit the disclosure. It will be appreciated that it is within the scope of the disclosure that individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method for monitoring a moving conveyor belt comprising a first edge region, a second edge region, and a load carrying region in a conveyor belt system, to detect belt damage, changes in belt width, and changes in belt tracking;

wherein the method comprises monitoring a magnetic field associated with a plurality of edge detection inserts embedded within the conveyor belt utilizing a magnetic sensor system to detect the magnetic field of the edge detection inserts, wherein the edge detection inserts are positioned longitudinally along the length of the conveyor belt in the first edge region and the second edge region of the conveyor belt, and wherein the edge detection inserts contain a plurality of magnetically permeable wires, and, wherein the plurality of magnetically permeable wires are aligned within the edge detection inserts at a bias angle of 15° to 75° from being perpendicular to the longitudinal direction of the belt.

2. The method for monitoring a moving conveyor belt as specified in claim 1, wherein the conveyor belt includes steel reinforcements and belt splices, and wherein the conveyor belt is monitored for reinforcement damage and splice damage by monitoring images of the magnetic fields associated with the steel reinforcements.

3. The method for monitoring a moving conveyor belt as specified in claim 2, wherein the images of the magnetic fields extend over an entire length of the conveyor belt.

4. The method for monitoring a moving conveyor belt as specified in claim 1, wherein the plurality of permeable wires are aligned within the edge detection inserts at a bias angle of 25° to 65° from being perpendicular to the longitudinal direction of the belt.

5. The method for monitoring a moving conveyor belt as specified in claim 4, wherein the plurality of permeable wires are aligned within the edge detection inserts at a bias angle of 35° to 55° from being perpendicular to the longitudinal direction of the belt.

6. The method for monitoring a moving conveyor belt as specified in claim 1, wherein the conveyor belt is comprised of a multitude of edge detection inserts embedded within a first edge region and a second edge region, and wherein the first edge region and the second edge region of the conveyor belt do not extend across more than 45% of the total width of the conveyor belt.

7. The method for monitoring a moving conveyor belt as specified in claim 6, wherein the first edge region and the second edge region of the conveyor belt do not extend across more than 30% of the total width of the conveyor belt.

8. The method for monitoring a moving conveyor belt as specified in claim 7, wherein the first edge region and the second edge region of the conveyor belt do not extend across more than 25% of the total width of the conveyor belt.

9. The method for monitoring a moving conveyor belt as specified in claim 8, wherein the first edge region and the second edge region of the conveyor belt do not extend across more than 25% of the total width of the conveyor belt.

10. The method for monitoring a moving conveyor belt as specified in claim 1, wherein the conveyor belt comprises magnetic rip detection inserts embedded within a center region of the belt.

11. The method for monitoring a moving conveyor belt as specified in claim 10, wherein the magnetic rip detection inserts embedded within a center region of the belt are between 30 to 50 centimeters wide.

12. The method for monitoring a moving conveyor belt as specified in claim 1, wherein the edge detection inserts are between 12 centimeters to 17 centimeters wide.

13. The method for monitoring a moving conveyor belt as specified in claim 2, wherein the edge detection inserts are incrementally spaced along the longitudinal edges of the moving conveyor belt.

14. The method for monitoring a moving conveyor belt as specified in claim 1, wherein the moving conveyor belt further comprises corrugated walls, wherein a first corrugated wall is situated between the load carrying region and the first edge region of the conveyor belt, and wherein a second corrugated wall is situated between the load carrying region and the second edge region of the conveyor belt.

15. The method for monitoring a moving conveyor belt as specified in claim 1, wherein the moving conveyor belt is a bucket conveyor belt, and wherein the bucket conveyor belt comprises a plurality of buckets which are situated within the load carrying region of the conveyor belt.

\* \* \* \* \*